United States Patent [19]

de Buck van Overstraeten

[11] 4,115,615
[45] Sep. 19, 1978

[54] FABRIC PERMEABLE TO ULTRAVIOLET RADIATIONS

[75] Inventor: Jean-Pierre de Buck van Overstraeten, Zwijnaarde, Belgium

[73] Assignee: Uvetex Glarus AG., Glarus, Switzerland

[21] Appl. No.: 793,550

[22] Filed: May 4, 1977

[30] Foreign Application Priority Data

May 10, 1976 [BE] Belgium .................................. 166902

[51] Int. Cl.$^2$ ........................ A41D 7/00; D03D 15/00
[52] U.S. Cl. ........................................... 428/229; 2/67;
2/243 A; 8/2.5 A; 101/470; 139/420 R;
428/397; 428/409; 428/474; 428/480
[58] Field of Search .............. 428/195, 196, 207, 229,
428/397, 474, 480, 395, 409, 918; 2/7, 411, 67,
243 A; 156/148, 167, 181, 244, 296; 264/103,
177 F; 139/420 R, 425 R; 101/470; 8/2.5 A

[56] References Cited

U.S. PATENT DOCUMENTS

| 2,391,959 | 1/1946 | Gallowhur ............................ 2/67 X |
| 2,444,492 | 7/1948 | Blout et al. ...................... 428/474 X |
| 3,147,582 | 9/1964 | Scharf ................................. 156/148 |
| 3,503,106 | 3/1970 | Port et al. ...................... 139/420 R |

FOREIGN PATENT DOCUMENTS 1,389,659  4/1975  United Kingdom.

*Primary Examiner*—William A. Powell
*Assistant Examiner*—M. G. Wityshyn
*Attorney, Agent, or Firm*—Brumbaugh, Graves, Donohue & Raymond

[57] ABSTRACT

This invention relates to a fabric made from a polymer or of a miXture of polymers having an absorption curve of radiating energy characterized by a minimum absorption between 3,200 A and 4,000 A and an important filtering below 3,200 A, said polymer being eXtruded at a speed allowing an eXtremely quick cooling such that the formation of large crystallites is inhibited while promoting proliferation of crystallites of very small sizes.

11 Claims, No Drawings

FABRIC PERMEABLE TO ULTRAVIOLET RADIATIONS

The invention relates to improvements to synthetic fabrics allowing the skin to become brown under bathing wear, under beach wear and light dresses, through windscreens and the like.

The study of the phenomenon of the skin bronzing or tanning supposes the study of the selection of the effective ultraviolet radiation. The efficiency around 3,000 A is very important. Two reasons limit its importance for bronzing.

The sun radiation of this wave length is strongly filtered by the atmosphere; this is such a radiation which is responsable for the skin erythema. It can be said that radiations between 3200 and 4000 A are the tanning or bronzing radiations causing rise of skin pigments, while radiations of 2,800 to 3,200 A are the burning radiations. Even at a low ratio, these burning radiations are particularly unpleasant. They cause sun burns. The sun creams intend to decrease the overall radiation intensity and more particularly to cut the radiation below 3,200 A in order to prevent burns. A small amount of burning radiation is however necessary in order to initiate or catalyze the action of browning radiations.

The problem consists thus of manufacturing a fabric which is broadly permeable to a narrow range of radiations, between 3,200 and 4,000 A, able to allow a greatly weakened amount of radiations below 3,200 A to pass, and opposing the radiations passage above 4,000 A. A fabric which does not meet this latter standard would be transparent.

Some existing fabrics, the material of which is completely opaque and thus opposes the radiation passage, as well of ultraviolet radiation as of visible radiation, such as cotton for example, have been specially made to this end by providing mesh openings, namely by providing open spaces which are large enough between the threads. They are light and transparent and generally they are not acceptable for normal manufacture of garments. A covering effect is obtained by using concealment effects due to configuration of some designs in contrasting colors.

The object of the invention consists on the contrary not in using the transparency phenomenon due to the presence of mesh openings, that is to say that according to the invention, one proposes a covering fabric having body enough and a mechanical strength of the normal kind in garment manufacture, this fabric being acceptable from the decency point of view. According to the invention, such a fabric allows browning radiations to pass while strongly filtering radiations causing erythema to appear. This is the addition of the various steps of the fabric manufacture process, which allows the desired effect to be obtained.

In order to allow the invention to be better understood, it is to be noted that when radiations strike a fabric, they are:

(1) partly reflected inwardly
(2) partly absorbed
(3) partly allowed to pass through meshes or openings
(4) partly reflected outwardly
(5) partly diffracted and diffused into the fabric material
(6) partly refracted.

Only the radiation fraction under 1 and 2 may be considered as being negative. The other ones are positive, most of radiation reaching the reverse side under different angles. Radiations mentioned under 4 to 6 inclusively are actually partly polarized. Experience has shown that said polarized radiations are particularly favourable to the skin browning phenomenon.

The fabric according to the invention has thus to be made by using a filament composed of a polymer to be selected by taking the previous conditions into account. The refracted radiation in the fabric also comprises an amount of polarized radiation, mainly in the case the filament has been drawn and has thus anisotropic crystallographic qualities.

To manufacture a fabric having hereinbefore mentioned specifications and which does not show drawbacks such as cited, this fabric will be made according to the invention from a polymer or a polymer mixture having an absorption curve of radiating energy characterized by a minimum absorption between 3,200 and 4,000 A and an important filtering below 3,200 A, said polymer being extruded at a speed allowing an extremely quick cooling such that the formation of large crystallites is inhibited while promoting proliferation of crystallites of very small sizes, the used yarn being furthermore composed of a very low number of strands, this fabric being woven or knitted so as to minimize air/polymer interfaces.

According to a preferred embodiment, the fabric according to the invention is made by using a yarn having a very reflecting surface.

Another characteristic is the fact that the fabric may be made by using a yarn having a flattened cross-section.

More particular properties can be reached from a fabric prepared by using a yarn made from polyamide 6, polyamide 66, polyester or polyvinyl chloride.

A step which is particularly favourable to reach the purpose of the invention consists of printing the fabric, preferably in thin layer, while suppressing addition of pigment particles in the filament material.

Other details and advantages of the fabric according to the invention will become apparent from the description of a fabric according to the invention, which will be given hereinafter; said description is only given by way of an example and does not limit the invention.

The synthetic fabric, which is noteworthy for its properties in relation with permeability to radiating energy is manufactured by weaving or knitting a yarn the strands of which are in an exceptionally low number. On the other hand, monofilament or strand crystallography must be such that refraction and diffraction of ultraviolet radiations are promoted by a proliferation of small crystallites while formation of large crystallites is inhibited.

The selection of the polymer having regard to the filtering of ultraviolet radiation is an important step on the way to the solution which is searched, as mentioned hereinbefore. The selection has been made amongst polymers which do not absorb radiations between 3,200 and 4,000 A, leaving to coloration made later to cause opacity, while selecting these polymers with an effective filtering characteristic below 3,200 A. Various polymers have acceptable characteristics. This is the case of nylon 6, nylon 66, polyester and polyvinyl chloride. The spinning possibilities of the latter polymer have been described in Belgian Pat. Nos. 718,606, 682,755, 689,244, 682,756 and 689,793. These non limitative references are given as examples. Polyamides 6 and 66 have the best absorption curves and as it is known these polymers spin very well.

Crystallographic morphology, use of stabilizers and mixing rate of the constituents must be such that particles of the latter are not the origin of crystallisation seeds which could create later crystallites of large sizes. In this connection, it has not to be forgotten that crystallisation occurs below melting temperature and that this crystallisation may be obtained as an increase of crystallite sizes or as development of new seeds. These are the large crystallites which must be avoided. These crystallites grow at a higher temperature than the formation temperature of the seeds. When the crystallisation rate is not too high, it is possible to keep this development under control and to suppress formation of crystallites of prohibitive sizes while promoting a large number of crystallites of small sizes. This is the case with polyamide 6 which must be cooled after spinning exactly below the critical temperature. The spinning speed must obviously be high enough.

In the case of polyamide 66, the crystallisation rate of which is higher, it is necessary to use means able to delay this crystallisation. The result is easily obtained by adding to the mixture some amount of polyamide 6 or any other crystallisation inhibition. The temperature will be decreased below temperature corresponding to a high formation rate of large crystallites while promoting, on the contrary, large amounts of seeds of small sizes to be formed.

It is advisable, during further operations such as coloration, texturisation or drawing, that in no case the temperature is increased above the critical crystallisation temperature.

It is obvious that use of pigments and of most of light or ageing stabilizers must be prohibited due to the fact that pigments, as stabilizers, have a high absorbing power. Amongst light stabilizers, sodium or potassium bromides are substantially the only ones which not only have no detrimental effect in this connection but may be considered as promoting permeability to ultraviolet radiations.

Tests have shown that absorption of ultraviolet radiations mainly occurs at the interfaces, namely at the boundary separating polymer yarns from air. An object of the invention is thus to prevent such interfaces. Transparency of a film to ultraviolet radiations can be excellent while transparency of a fabric having the same composition is substantially null. Use of monofilaments, which prevents successive contacts at the interfaces, seems to be advisable. But as use of monofilaments is excluded, use of yarns having a reduced number of strands is proposed.

It has been found that surface roughness is an important absorption factor. A yarn when used must thus be smooth and must give an irradiation effect under light. This irradiation increases the amount of polarized radiations through reflection.

From the preceding, it will be concluded that the covering effect of the fabric must be maximum with a minimum material having minimum interfaces, yarns of which the fabric is made having a maximum reflecting surface, crystallographic structure of the yarns being characterized by the presence of a very large number of crystallites of very small sizes and by the absence of crystallites having large sizes.

The maximum covering effect to be obtained with a minimum material is advantageously reached when manufacturing the fabric as a knitted article. The fabric finishing giving it necessary optical qualities cannot be made by using solutions based on pigments because the latter have a too high opacity to ultraviolet radiation. Coloring materials on the contrary act as filters for some determined wave lengths. The tendency of coloring materials to monochromatism determines purity of colors. There is thus a contradiction with the purpose aimed at: coloring material allows a color to pass and absorbs other radiations which are wished to pass through the fabric. There is a number of coloring materials having the property to allow some colors to pass while allowing passage of ultraviolet radiation.

Notwithstanding properties of some coloring materials, the latter are present in the yarn mass where they form a barrier to the passage of ultraviolet radiation.

The opacifying layer due to presence of pigments may be substantially decreased with respect to a pigmentation in the mass by deleting the coloration process and by finishing on the contrary the fabric by means of a printing process, more particularly for example a so-called "subli-static" printing.

It will be noted that the effect aimed at can be highly increased by searching a psychological effect based on more or less strong contrasts of colors and varied designs. In order to get the necessary covering effect, it may be sufficient to print some points only as it is produced when making a screened negative giving an impression of filled surfaces while actually only a relatively small fraction of the surface is covered and is responsible for the covering effect. Printing in very thin layers perfectly allows this purpose to be reached.

The fabric according to the invention is thus made by using yarns and finished by techniques having for their object to allow some range of ultraviolet radiations to pass and to cause their refraction, their reflection or their diffraction towards the skin, thanks to the internal crystallographic structure of yarns, the surface structure of the latter and the configuration of the fabric itself.

Practical tests have shown that skin browning or tanning under a fabric according to the invention and such as hereinbefore described is not only of high level but also similar to that such as obtained when using a sun cream of good quality. Thus carrying garments, made by means of fabrics according to the invention, improves tanning while preventing burns.

The invention is not limited to the embodiment such as described and many modifications may be brought thereto without departing from the scope of this patent application.

I claim:

1. A fabric, which is made from yarn of a polymer or a polymer mixture having an absorption curve of radiating energy characterized by a minimum absorption between 3,200 and 4,000 A and an important filtering below 3,200 A, said polymer being extruded at a speed allowing an extremely quick cooling such that the formation of large crystallites is inhibited while proliferation of crystallites of very small sizes is promoted, said yarn being furthermore composed of a very low number of strands, and said fabric being woven or knitted so as to minimize air/polymer interfaces.

2. A fabric as claimed in claim 1, wherein the yarn has a substantially reflective surface.

3. A fabric as claimed in claim 1, wherein the yarn has a flattened cross-section.

4. A fabric as claimed in claim 1, wherein the yarn is made of polyamide 6.

5. A fabric as claimed in claim 1, wherein the yarn is made of polyamide 66.

6. A fabric as claimed in claim 1, wherein the yarn is made of polyester.

7. A fabric as claimed in claim 1, wherein the yarn is made of polyvinyl chloride.

8. A fabric as claimed in claim 1, wherein the fabric has a design printed thereon.

9. A fabric as claimed in claim 8, wherein said printed design is made in a thin layer.

10. A fabric as claimed in claim 8, wherein said printed design is made by subli-static printing.

11. A fabric as claimed in claim 8, wherein said printed design is made by using contrasting colors thereby providing a concealing effect.

* * * * *